United States Patent [19]

Hershberger et al.

[11] Patent Number: 4,898,828

[45] Date of Patent: Feb. 6, 1990

[54] ULTRAHIGH COPY NUMBER STREPTOMYCETES PLASMIDS

[75] Inventors: Charles L. Hershberger, New Palestine; Jeffrey L. Larson; Patricia A. Reynolds, both of Indianapolis, all of Ind.

[73] Assignee: Eli Lilly and Company, Indianapolis, Ind.

[21] Appl. No.: 841,920

[22] Filed: Mar. 20, 1986

Related U.S. Application Data

[63] Continuation-in-part of Ser. No. 763,172, Aug. 7, 1985, abandoned.

[51] Int. Cl.[4] .................. C12N 1/20; C12N 15/00; C07H 21/04
[52] U.S. Cl. .......................... 435/252.3; 435/172.3; 435/252.33; 435/252.35; 435/320; 536/27; 935/6; 935/29; 935/73; 935/75
[58] Field of Search .............. 435/68, 70, 71, 91, 435/172.1, 172.3, 243, 253, 320, 252.3, 252.31–252.35; 536/27; 935/6, 29, 73, 75

[56] References Cited

U.S. PATENT DOCUMENTS 4,752,574  6/1988  Hershberger et al. ................. 435/34
4,753,886  6/1988  Hershberger et al. ............... 435/253

OTHER PUBLICATIONS

Maniatis et al., 1982, Molecular Cloning: A Laboratory Manual, Cover Page and pp. 133–134.
Bethesda Research Laboratories 1985 Catalogue, Cover Page and p. 51.
Bibb, M. J. et al., 1977, *Molec. Gen. Genet.,* 154:155–166.
Bibb, M. J. et al., 1980, *Nature,* 284:526–531.
Thompson, C. J. et al., 1982, *Gene,* 20:51–62.
Thompson, C. J. et al., 1982 *J. Bacteriol.,* 151:668–677.
Schrempf and Goebel, 1977, *J. Bacteriol.,* 131:251–258.
Hershberger, C. L. et al., 1983, "Uses of Recombinant DNA for Analysis of Streeptomyces Species", *Ann. N. Y. Acad. Sci.,* Venkatasubramonian, Constantinices, and Vieth, eds., pp. 31–46.
Larson and Hershberger, 1984, *J. Bacteriol.,* 157:314–317.
Manis and Highlander, 1982, *Gene,* 18:13–20.
Nordstrom, K., 1985, "Control of Plasmid Replication: Theoretical Considerations and Practicel Solutions", *Plasmids in Bacteria,* Helinski, Cohen, Clewell, Jackson and Hollaender, eds., pp. 189–214, Plenum Press, N. Y.

*Primary Examiner*—James Martinell
*Attorney, Agent, or Firm*—Douglas K. Norman; Leroy Whitaker

[57] ABSTRACT

The present invention discloses an ~1.4 kb BclI-Sau3A restriction fragment containing the minimal replicon of the *Streptomyces coelicolor* plasmid SCP2*. This minimal replicon was deduced from plasmid derivatives constructed by in vitro deletions and has been identified as the smallest, self-replicating segment of the SCP2* plasmid. The minimal replicon specifies an ultrahigh level of plasmid DNA (more than 1000 fold increase from the basic replicon) when vectors containing this sequence are transformed into *Streptomyces lividans*. This replicon can be used to construct smaller, more efficient recombinant DNA shuttle vectors to clone DNA into streptomycetes.

30 Claims, 12 Drawing Sheets

ULTRAHIGH COPY NUMBER STREPTOMYCETES PLASMIDS

Cross Reference

This application is a continuation-in-part of our co-pending U.S. Application Ser. No. 763,172, filed Aug. 7, 1985.

BACKGROUND

SCP2 is a sex factor from *Streptomyces coelicolor* and SCP2* is a mutant with enhanced pock formation which associates with sex factor activity in streptomycetes. These low copy number plasmids can be transferred to a variety of streptomycetes by genetic crosses and protoplast transformations. Much of the plasmid DNA is not essential for replication or use of the replicon in vectors for recombinant DNA. The present invention extends the knowledge about SCP2* to derive several small, self-transmissible plasmids, identify a fragment containing the basic replicon which contains the necessary information for normal replication, identify DNA segments controlling the level of plasmid DNA, and identify the minimal replicon which is the smallest self-replicating segment of the plasmid.

SUMMARY OF THE INVENTION

The present invention discloses a variety of recombinant DNA cloning vectors comprising a minimal replicon of SCP2*, one or more DNA segments that convey resistance to at least one antibiotic when transformed into a sensitive, restrictionless host cell and, in the case of shuttle vector constructions, an *E. coli* replicon. The vectors contain a truncated streptomycete replicon which increases the copy number of plasmids containing the truncated, minimal replicon relative to plasmids containing the wildtype replicon of SCP2*. The invention further comprises transformants containing the aforementioned vectors.

The present invention provides selectable, ultrahigh copy number plasmids of more than 1000 copies per cell for use in streptomycetes and related host cells. Heretofore, the development and exploitation of recombinant DNA technology in streptomycetes has been retarded and made especially difficult because of the general lack of functional ultrahigh copy number vectors. Previously, low copy number vectors (1–5 copies per chromosome), moderate copy number vectors (5–50 copies per chromosome), and high copy number vectors (50–1000 copies per chromosome) were available. The existence of ultrahigh copy number plasmids provides a means by which the product yield of proteins encoded by genes carried on these ultrahigh copy number plasmids may be dramatically increased when compared to the level of expression from genes carried on any of the previously characterized copy number plasmids. Thus, ultrahigh copy number plasmids are advantageous for obtaining high level expression of non-toxic gene products. Cloning a gene into an ultrahigh copy number vector may provide high level accumulation of the gene product because most but not all genes express the protein proportional to the gene copy number.

Deletion analysis of the present vectors containing segments of SCP2* provide restriction site maps of SCP2* derivatives that are disclosed in FIG. 1 of the accompanying drawings. The SCP2* minimal replicon has been identified as an ~1.4 kilobase (kb) BclI-Sau3A restriction fragment that specifies an ultrahigh level of plasmid DNA (over 1000 copies per chromosome).

Additional cloning vectors were developed as part of the studies to identify the minimal replicon of SCP2*. The replicon probe vector pHJL10 is useful to isolate replicons from a variety of streptomycetes while the shuttle vectors pHJL225, pHJL400, and pHJL401, which incorporate a smaller SCP2* replicon that specifies moderate plasmid DNA level in streptomycetes, are useful for shotgun cloning of genomic DNA.

The present vectors are particularly useful because they are relatively small, versatile, and can transform and be selected in any streptomycete cell that is sensitive to an antibiotic for which resistance is conveyed and wherein the truncated replicon provides sufficient information for self-replication. Since more than seventy percent of naturally occurring antibiotics are produced by streptomycetes strains, it is desirable to develop cloning systems and vectors that are applicable to that industrially important group. The present invention provides such vectors and thus allows for the cloning of genes into streptomycetes both for increasing the yields of known antibiotics as well as for the production of new antibiotics and antibiotic derivatives.

For purposes of the present invention, as disclosed and claimed herein, the following terms are as defined below.

Ap or ApR—the ampicillin-resistant phenotype or gene conferring same.

Basic replicon—the smallest piece of DNA that replicates with the wildtype copy number.

Km—the kanamycin-resistant phenotype or gene conferring same.

NmR or aph—the neomycin-resistant phenotype or gene conferring same.

Pleiotropic—the production of multiple, and apparently unrelated, copy number effects by a single replicon.

Recombinant DNA Cloning Vector—any autonomously replicating agent, including, but not limited to, plasmids and phages, comprising a DNA molecule to which one or more additional DNA segments can be or have been added.

Recombinant DNA Expression Vector—any recombinant DNA cloning vector into which a promoter has been incorporated.

Replicon—a DNA sequence that controls and allows for autonomous replication of a plasmid or other vector.

Restriction Fragment—any linear DNA sequence generated by the action of one or more restriction endonuclease enzymes. Sensitive Host Cell—a host cell that cannot grow without a DNA segment encoding a selectable resistance characteristic.

Transformation—the introduction of DNA into a recipient host cell that changes the genotype of the recipient host cell.

TsR or tsr—the thiostrepton-resistant phenotype or gene conferring same.

DETAILED DESCRIPTION OF THE INVENTION

Figure 1:
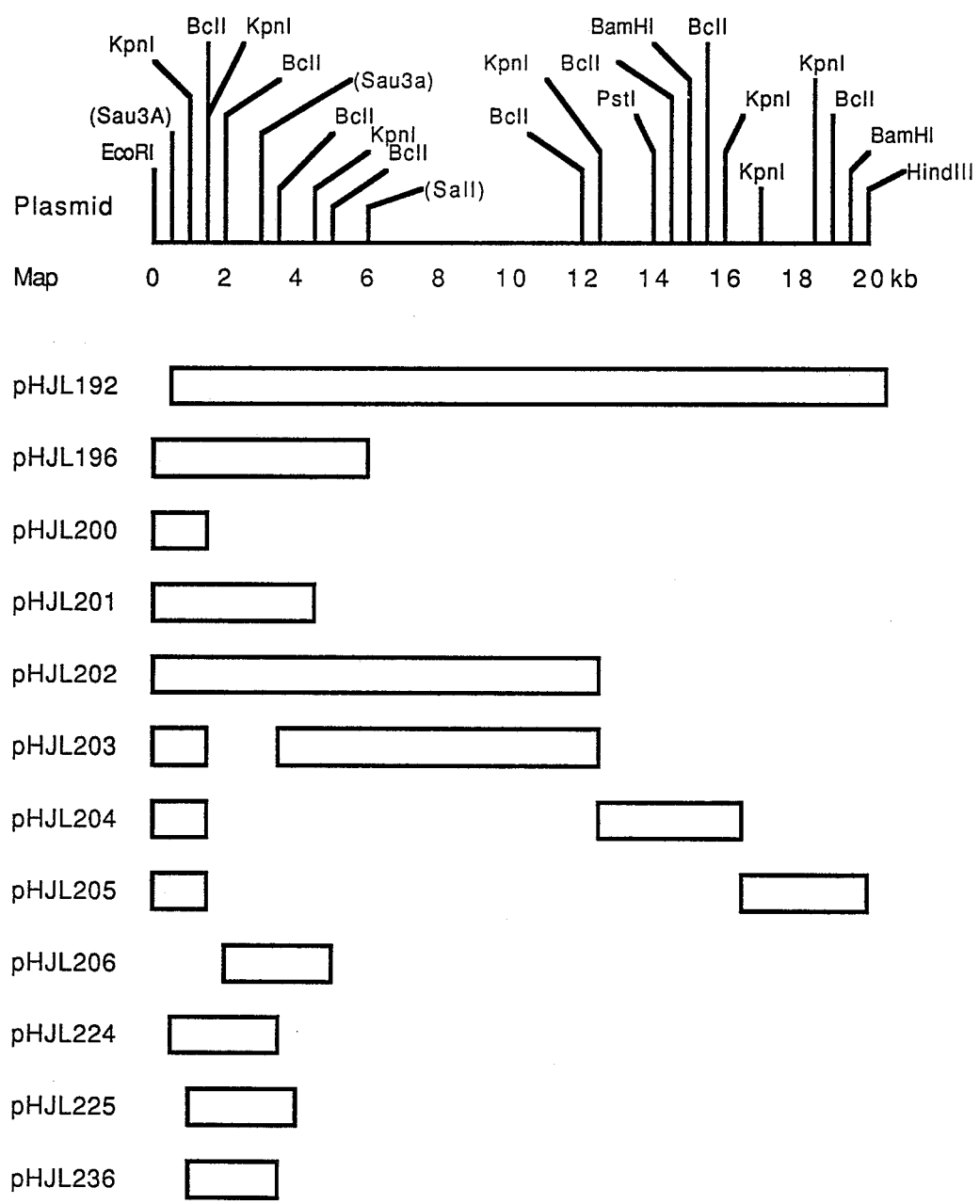
FIG. 1 illustrates deletion derivatives of the SCP2* portion of plasmid pHJL192. The top line shows a linear restriction map of SCP2* opened at the EcoRI and HindIII sites. Restriction sites in parenthesis are not unique. The black bars identify the portions of SCP2* contained in the plasmids named at the left end of the bar. The segments may be identified by aligning the bar with the restriction map of the SCP2* portion of pHJL192 on the top line.

The present invention provides an SCP2* minimal replicon DNA sequence that confers a plieotriopic copy number phenotype to plasmids transformed into different strains of streptomycetes. Depicting only one strand of the DNA sequence for convenience, the novel SCP2* minimal replicon comprises the sequence:

```
              10         20         30         40         50
5'-TGATCAATGG CGGGGGAATC GACCTCAGCC ACAGAAAGGC AACCCCTGCG 60         70         80         90        100
   GCGGGGGCGA CAACGGCGGC GGTACGGAGG TACCTCAGCC GCCCACCGGC 110        120        130        140        150
   AGGACGACGC TTCCTTCCTG CTTGTGGCCG GCCGAGGACA GCGTGCGGTC 160        170        180        190        200
   GCTAGGCGTG ATCAGGTGGC ATCAGTCGGG ACCCGCAAGC CCGCCAGGGC 210        220        230        240        250
   CGAGGACTCG CCGACCGTAG GCGCCGACGA GGACCAGGTG CGCAGGACCG 260        270        280        290        300
   CCGGCCTTCC CCGTAGAAGC TAAGAGCGGC CCGGTATGCC GGGCGGGTAG 310        320        330        340        350
   GAGTCCAGGG CGGTCACCAC GGTGTGCGCC GTGGTGCGCG AGTGACGGCG 360        370        380        390        400
   CGCGCCTTCT AGTGAAGAAG GGGCGCATGC TCTTGACCTG GTAAAACGCG 410        420        430        440        450
   CGGCTAAGCG GCTAAAAACC GCCGGTTACT GGGTCAAAAA TCGCCGCTTA 460        470        480        490        500
   GCTACCCACC GTGCGTCCCT CGTCGCGCCC GGTCGCCAGG AAGTCGCGTC 510        520        530        540        550
   ACCTATGCGT GTGACACGCG GACTAAGCGG CTGTTTTTCG GAGTGGTGAC 560        570        580        590        600
   CTGTTAGTTT CCTCTCGTAA GCGGCGGTTC ATCGGAGCTA AGGGGTCAAA 610        620        630        640        650
   AACCGCCCCT TAGCGCGAGG ATGGGAGAGG CGCGAGTGCC GACGAGGAAG 660        670        680        690        700
   CGCGGGCCGA ACATGGCCCT GGTCAACATG GACACCGGAG AGGCGGTGTC 710        720        730        740        750
   CGCCAGGCCG CGGACTCCGC ACCAGTTCGA CGGGAAGGGG TACACCTTGC 760        770        780        790        800
   AGGCCGTAGG CAGCGACGTC CCCCTGTACT CCCTCGGGCT GGCCGCAGCG 810        820        830        840        850
   GAGTGGGCGA CGCTCGAATG GCTCCGCGAA CACGGAGGCG CGGCCGGATA 860        870        880        890        900
   CGTCCCGGTC ACGCCCGAGG AGCTGGGCGA GGACGTCGGC GCCAGCAAGG
```

```
       910        920        930        940        950
ACACCTGCCG GAAGGCCCTT AACCGGCTGG TCAAGCTCGG GCTTGTGGTC 960        970        980        990       1000
AAGCCGGGCC CGCGATCCGG CTCTTACCAG CTGAACCCCC TCCGATACTG 1010       1020       1030       1040       1050
GGAGGGAGCC GGGAGCACGC AGGTCAACGC CTGCCGCCGC ATGGCGCCGC 1060       1070       1080       1090       1100
CGCGTGTGGC CCCGGACGAC AAGGCCATGA CCAGGTCCGC CAGCAAGCCC 1110       1120       1130       1140       1150
AAGACCATCC CGGCTACCCG CCGCCGCGCC GCAGGAGAGA CGCGATGACG 1160       1170       1180       1190       1200
ACCATGCCCG TAGAAGGCTT CAACCCGGAG CGCGACCTGA CCGCCCCGTC 1210       1220       1230       1240       1250
GCTGTACTCG CCGAACCTGT CCGCCGCTCA GCACTGCACG CTCGCGTGGG 1260       1270       1280       1290       1300
TGGAGGACCA CGGCGGCCTG TTTGACGTCA TCCCCGTACC GGTCGAAACC 1310       1320       1330       1340       1350
GTCGCCGAGG ACTGCGGCAA CTCCGTCTCC ACGGTGCACG AGGCTCTCGC 1360       1370       1380       1390       1400
CCGCCTGGAG GCCCTGAACC TCCTCGTGCG GACCTCCGCC GGCCTCTACC

1405
GGATC-3'
``` wherein
- A is deoxyadenyl,
- C is deoxycytidyl,
- G is deoxyguanyl, and
- T is thymidyl.

The invention further comprises novel recombinant DNA streptomycetes vectors comprising:

(a) a DNA sequence conferring a pleiotropic copy number phenotype and having at least the SCP2* minimal replicon sequence, and (b) one or more DNA segments that convey resistance to at least one antibiotic when transformed into a sensitive, restrictionless host cell.

The invention also comprises shuttle vectors and transformants of the aforementioned vectors.

Vectors of the present invention are constructed through enzymatic digestion of plasmid pHJL192. Plasmid pHJL192 is also designated pJL192 herein. The various digestions that are taught herein result in the identification and isolation of the ~1.4 kb BclI-Sau3A miminal replicon fragment. This fragment can then be ligated to a streptomycetes antibiotic resistance-conferring gene, as well as to a functional replicon-containing and antibiotic resistance-conferring restriction fragment of an E. coli plasmid to produce self-replicating, bifunctional vectors that are selectable in both E. coli and streptomycetes.

Figure 2:
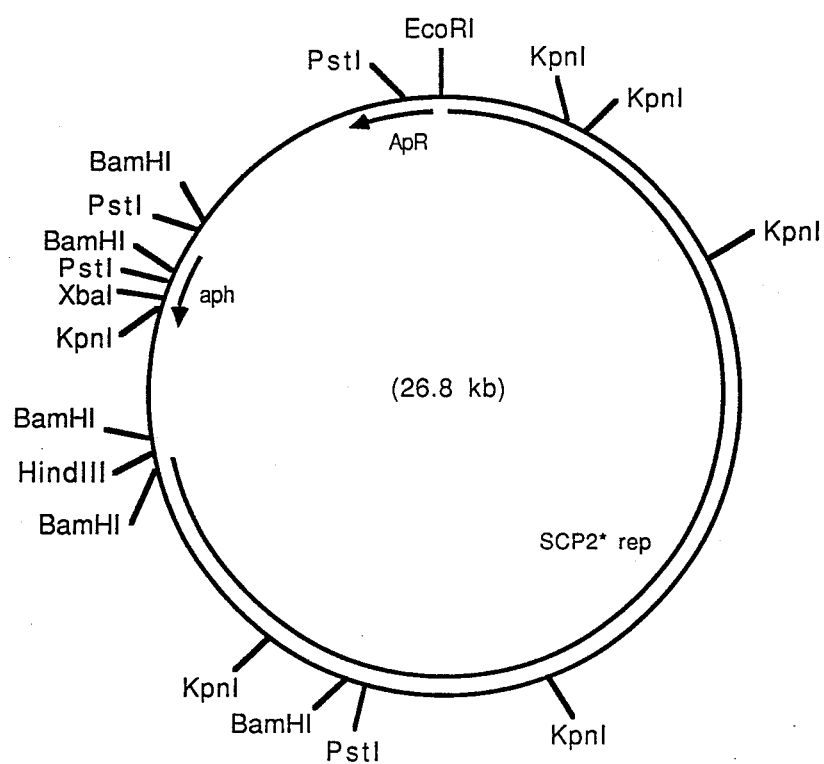
FIG. 2 is a restriction site map of plasmid pHJL192.

Plasmid pHJL192 can be conventionally isolated from E. coli K12 C600R$_k$—M$_k$—/pJL192, a strain deposited and made part of the Northern Regional Research Laboratory, Peoria, Ill. 61604. The strain is available to the public, as a preferred source and stock reservoir of the plasmid, under the accession number NRRL B-15040. A restriction site map of plasmid pHJL192 is presented in FIG. 2 of the accompanying drawings. For purposes of the present application, FIG. 2 and all subsequent figures are not drawn precisely to scale.

Plasmid pHJL192 contains an ~5.9 kb EcoRI-SalI SCP2* replicon fragment that contains all of the information necessary for normal replication. Deletion derivatives of plasmid pHJL192 provided the opportunity to derive a functional map of SCP2* and identify the sequences that are essential for plasmid replication. Partial digestion of pHJL192 with KpnI generated an array of linear products and T4 DNA ligase formed circular molecules that transformed E. coli K12 C600R$_k$—M$_k$—to ampicillin resistance. Restriction mapping identified the plasmids pHJL200-205. Plasmid pHJL201 transformed Streptomyces griseofuscus C581 (C581) to neomycin resistance and this transformed host exhibited substantially more plasmid DNA than C581 containing plasmid pHJL192. It is believed that the regulatory sequence controlling the SCP2* copy number was substantially mutated upon the paring down of the ~5.9 kb EcoRI-SalI replicon fragment of SCP2* to the ~4.5 kb EcoRI-KpnI SCP2* fragment of plasmid pHJL201.

Plasmids pHJL200-205 are disclosed in copending application, Hershberger and Larson, Ser. No. 639,566, filed Aug. 10, 1984 now U.S. Pat. No. 4,753,866, issued June 28, 1988. In addition, plasmids pHJL125, pHJL196, and pHJL197, which are useful and convenient plasmids for use in the present invention, are disclosed in copending application, Hershberger and Larson, Ser. No. 478,133, filed Mar. 23, 1983, now abandoned as well as in Larson and Hershberger, 1984, J. Bacteriol. 157:314. The teaching of these applications and reference are herein incorporated by reference.

Subcloning the ~2.9 or 3.0 kb KpnI fragment common to both pHJL201 and 202 into KpnI-digested pHJL5 generated plasmid pHJL206. Plasmid pHJL5 arose as a spontaneous deletion of pHJL192 but, in contrast to pHJL192, pHJL5 does not replicate in streptomycetes. Plasmid pHJL206 does replicate in C581 with a plasmid yield similar to pHJL201.

The next stage of replicon identification used a replicon probe vector that carries streptomycete resistance markers but is unable to replicate in streptomycetes.

Figure 3:
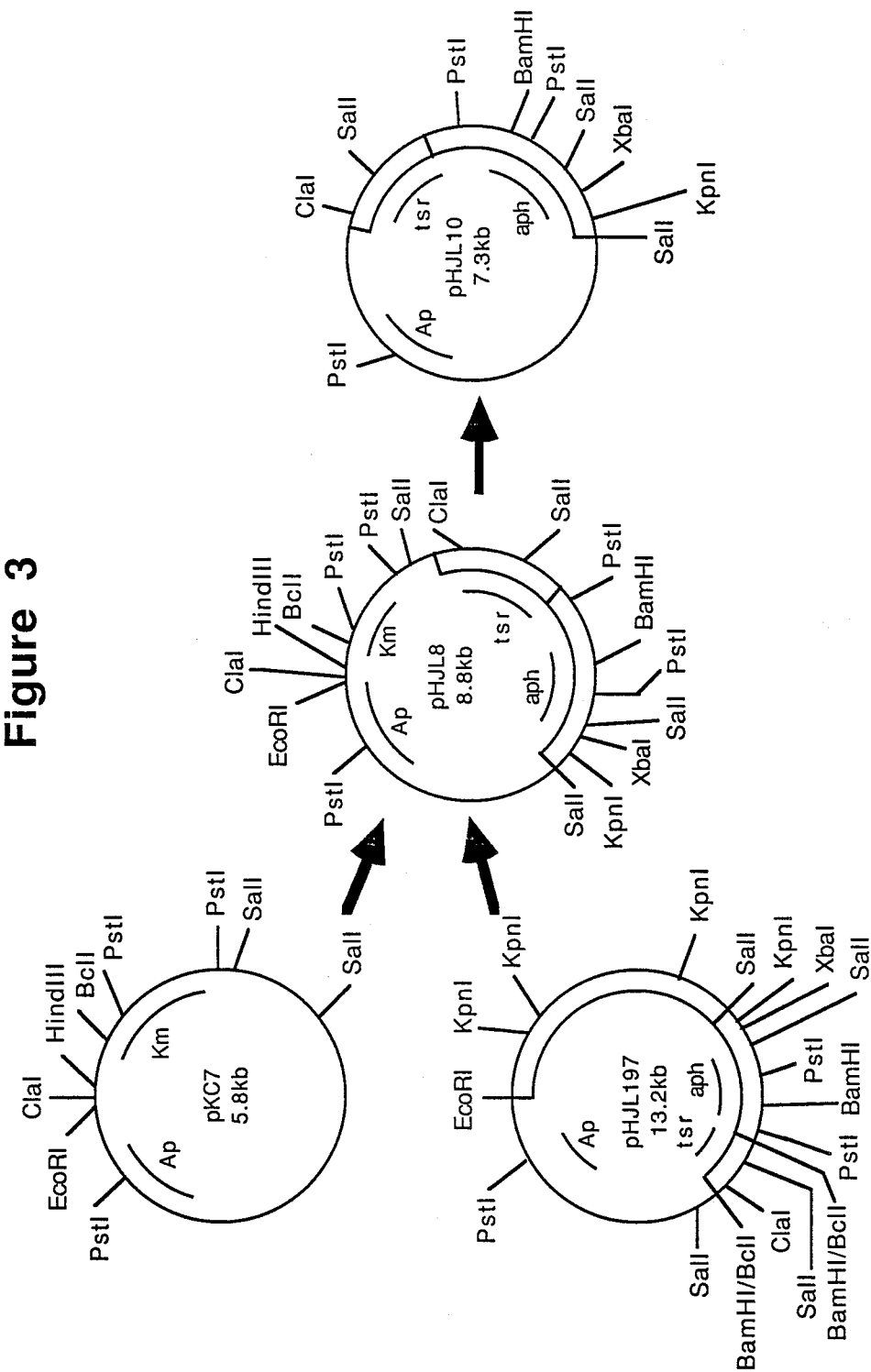
FIG. 3 illustrates the construction of replicon probes. The black bar identifies the segment from SCP2*. The open bar identifies the segment containing the aph gene for neomycin resistance. The cross-hatched bar identifies the segment containing the tsr gene for thiostrepton resistance. Plasmid pKC7 is the *E. coli* plasmid. Arrows identify the approximate location and direction of expression of genes for antibiotic resistance.

The construction of the replicon probe vectors is illustrated in FIG. 3 of the accompanying drawings. The ~5.2 kb SalI fragment of plasmid pKC7 (ATCC 37084) contains the kanamycin resistance gene of Tn5 and the ampicillin resistance gene and replicon of plasmid pBR322. Partial SalI digestion of plasmid pHJL197 released an ~3.6 kb fragment containing the neomycin resistance (aph) and thiostrepton resistance (tsr) genes for streptomycetes. T4 DNA ligase joined the purified fragments to produce pHJL8. The replicon probe vector pHJL8 was ligated to several streptomycete replicons and transformed C581 to thiostrepton resistance and neomycin resistance. As the instabilities of the Tn5 kanamycin gene in pHJL8 became apparent, the ~1.3 kb EcoRI-SalI fragment containing the Tn5 gene was deleted to produce pHJL10. T4 DNA polymerase filled in the EcoRI and SalI termini so that T4 DNA ligase circularized the linear plasmid by blunt-end ligation. Rescue experiments tested the usefulness of pHJL10. BamHI fragments of S. coelicolor DNA generated two TsR clones in C581. KpnI fragments of S. coelicolor DNA generated one NmR, TsR clone in C581. BamHI fragments of S. griseofuscus DNA generated two TsR clones in C581. Neither the restriction fragments nor self-ligated pHJL10 transformed C581 to antibiotic resistance; therefore, these experiments demonstrate the usefulness of pHJL10 to rescue replicons of streptomycetes.

Figure 4:
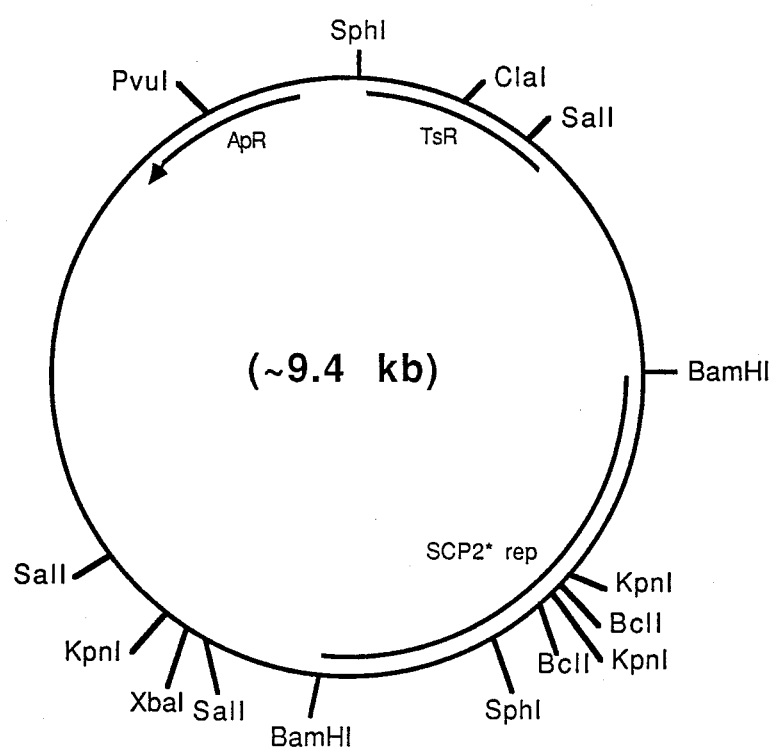
FIG. 4 is a restriction site and function map of plasmid pHJL224.
Figure 5:
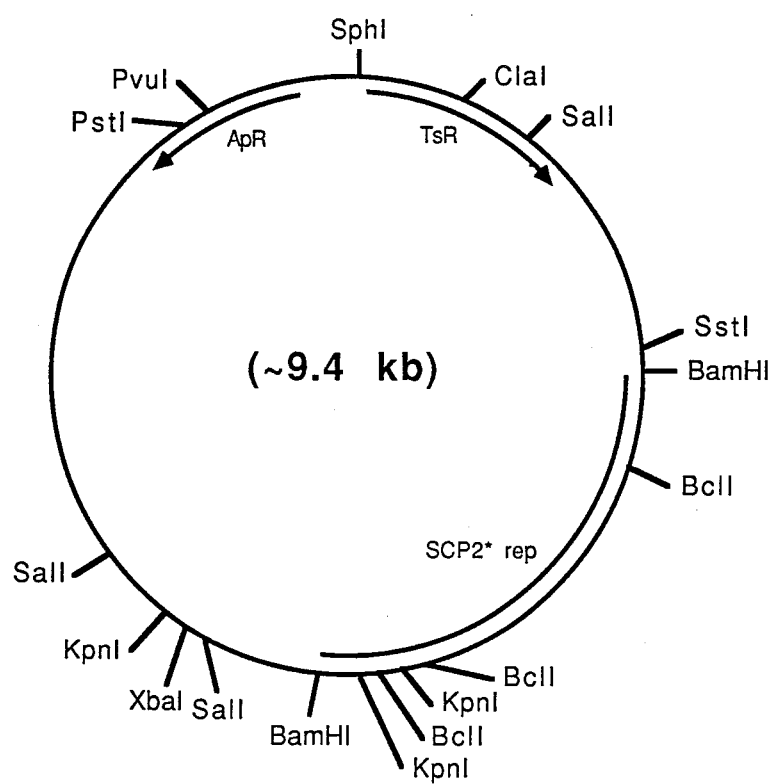
FIG. 5 is a restriction site and function map of plasmid pHJL225.

Shotgun cloning of random fragments into pHJL10 further delineated the SCP2* replicon. Sau3A digestion of the ~5.9 kb EcoRI-SalI fragment of pHJL125, which corresponds to the ~5.9 kb EcoRI-SalI fragment of pHJL192, generated an array of partial digestion products and T4 DNA ligase joined the fragments to BamHI-digested pHJL10. Thiostrepton resistant transformants of C581 provided the plasmids pHJL220-225. BamHi restriction enzyme excised an ~2.2 kb BamHI fragment from plasmids pHJL224 and pHJL225. The ~2.2 kb fragment is the smallest self-replicating fragment in the series. Since these exact configurations may not be easily reproducible, plasmids pHJL224 and pHJL225 have been deposited at the NRRL. The two strains E. coli K12 C600R$_k$—M$_k$—/pHJL224 and E. coli K12 C600R$_k$—M$_k$—/pHJL225 are available to the public, as a preferred source and stock reservoir of their respective plasmids, under the accession numbers NRRL B-15988 and NRRL B-18052. Restriction site and function maps of plasmids pHJL224 and pHJL225 are presented in FIGS. 4 and 5 of the accompanying drawings.

Figure 12:
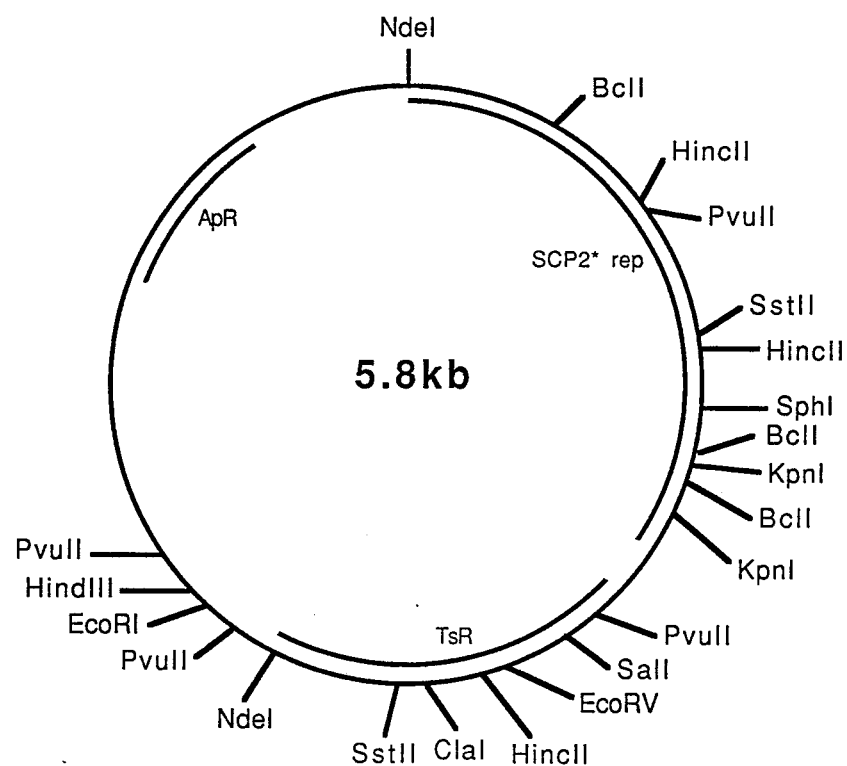
FIG. 12 is a restriction site and function map of plasmid pHJL400.

Plasmid pHJL225 provided the replicon to construct a small selectable plasmid for streptomycetes. T4 DNA ligase joined the ~2.2 kb BamHI restriction fragment of pHJL225 and an ~1.1 kb BclI fragment containing the thiostrepton resistance gene to produce the intermediate plasmid pHJL399. A shuttle vector was constructed from pHJL399 by digesting pHJL399 with NdeI restriction enzyme and ligating the linearized fragment to NdeI-digested pUC19, a commercially available plasmid containing a polylinker of unique restriction sites (Pharmacia, Inc., 800 Centennial Dr., Piscataway, N.J. 08854). The ligation mixture was used to transform E. coli to ampicillin resistance and streptomycetes to thiostrepton resistance. Plasmids of reverse orientation were isolated and designated pHJL400 and pHJL401. A restriction site and function map of the plasmid pHJL400, is presented in FIG. 12 of the accompanying drawings.

The levels of plasmid DNA in moderate copy number vectors are sufficiently high to isolate reasonable quantities of DNA for characterization and further manipulation. For this reason, the moderate copy number vector pBR322 (15–30 copies per cell in E. coli) and its derivatives are probably used more frequently than any other available vector. The moderate copy number vectors pHJL225, pHJL400 and pHJL401 are similarly useful vectors. Furthermore, given the broader host range capacity of plasmids pHJL400 and pHJL401, these vectors are more widely available for shotgun cloning. At moderate gene copy numbers, most gene products do not accumulate to inhibitory levels; therefore only the most toxic genes are lost from random genomic libraries. One skilled in the art will appreciate that the present cloning vectors are advantageous in obtaining expression of poorly transcribed or translated genes cloned into streptomycetes.

Comparison of the SCP2* segments in pHJL206 and pHJL224 identified an ~1.4 kb overlap (see FIG. 1). KpnI and BamHI digestion excised the ~1.4 kb mutual fragment from pHJL224. Substitution of the ~1.4 kb fragment for the 0.755 kb KpnI-BamHI fragment of pHJL10 produced pHJL236. Thiostrepton resistant transformants of S. lividans TK23 (TK23) containing pHJL236, yield 100 fold more plasmid DNA than similar cultures containing pHJL201 or 225 and 1000 fold more plasmid DNA than similar cultures containing pHJL192 or 197. Thus, plasmid pHJL236 is the first example of a streptomycete plasmid containing a replicon that specifies an ultrahigh level of DNA.

The SCP2* segment in pHJL236 was further analyzed to identify the minimal replicon. T4 DNA ligase joined the ~1.4 kb KpnI-BamHI fragment of pHJL236 to an ~1.9 kb KpnI-BamHI fragment containing the neomycin resistance gene from pHJL196. The new plasmid, pHJL241 transforms TK23 to neomycin resistance. T4 DNA ligase joined BamHI- and BclI-digested pHJL241 to the ~1.1 kb BclI fragment containing the thiostrepton resistance gene to produce pHJL250. Several copies of an 159 bp BclI fragment were present in pHJL250; these additional BclI fragments were removed during a BclI digestion of pHJL250. Circularization with T4 DNA ligase produced pHJL251 which contains a single copy of the 159 bp BclI fragment. Attempts to delete either the single 159 bp BclI fragment or an ~0.32 kb PvuII-BamHI fragment from the other end of the SCP2* segment in pHJL251 did not produce a functional replicon. Therefore, the ~1.4 kb BclI-Sau3A fragment in pHJL251 contains the minimal replicon of SCP2* that specifies an ultrahigh level of plasmid DNA.

A shuttle vector was constructed from pHJL251 and pUC18. T4 DNA ligase joined the plasmids at their unique NdeI sites to produce pHJL302, which transforms E. coli JM109 (a variety of Messing strains are commercially available from BRL) to ampicillin resistance and TK23 to thiostrepton resistance. Plasmid pHJL302 is a shuttle vector which confers the cloning advantages of pUC18 in E. coli and yields ultrahigh levels of plasmid DNA in Streptomyces lividans TK23.

While all the embodiments of the present invention are useful, some of the present recombinant DNA cloning vectors are preferred. Accordingly, preferred vectors are plasmids pHJL10, pHJL224, pHJL225, pHJL236, pHJL241, pHJL251, pHJL302, pHJL400, and pHJL401; and preferred transformants are S. lividans TK23/pHJL241, S. lividans TK23/pHJL251, S.

griseofuscus/pHJL400, S. griseofuscus/pHJL401, S. griseofuscus/pHJL302, S. lividans TK23/pHJL302, S. fradiae/pHJL400, S. fradiae/pHJL401, S. fradiae/pHJL302, E. coli K12 C600R$_k$—M$_k$—/pHJL302, E. coli K12 C600R$_k$—M$_k$—/pHJL400, E. coli K12 C600R$_k$—M$_k$—/pHJL401, S. lividans TK23/pHJL400, and S. lividans TK23/pHJL401.

The shuttle vectors, pHJL236 and pHJL302, of the present invention comprise replicons that are functional in E. coli and streptomycetes and therefore provide flexibility in the choice of hosts. Consequently, cloned DNA sequences can be shuttled into E. coli for construction of new plasmids, physical analysis, and for mapping of restriction sites and then shuttled back into streptomycetes for functional analysis and improvement of strains. This is particularly advantageous because amplification and manipulation of plasmids can be done faster and more conveniently in E. coli than in streptomycetes. For example, the present vectors can be amplified conventionally in E. coli K12 by growth with spectinomycin or chloramphenicol. This is not possible in the streptomycetes host system. In addition, since all the plasmid vectors contain resistance markers that are expressed in E. coli K12, recombinants are easily selected. Therefore, large amounts of plasmid DNA can be isolated conveniently and in a shorter time than that required for doing similar procedures in streptomycetes.

The recombinant DNA cloning vectors of the present invention are not limited for use in a single species or strain of streptomycetes. To the contrary, the vectors are broadly applicable and can be transformed into host cells of many streptomycetes taxa, particularly restrictionless strains of economically important taxa that produce antibiotics such as aminoglycoside, macrolide, β-lactam, polyether, and glycopeptide antibiotics and the like. Such restrictionless strains are readily selected and isolated from streptomycetes taxa (Cox and Baltz, 1984, J. Bacteriol. 159: 499) or by conventional procedures well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

The various replicon restriction fragments of plasmids pHJL192, pUC19 and the like, and also the various antibiotic resistance-conferring DNA segments can be modified to facilitate ligation. For example, molecular linkers can be provided to the replicon fragment, as well as to the particular resistance-conferring DNA segments, to generate specific sites for subsequent ligation. In addition, the origin of replication-containing restriction fragments can also be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose.

The recombinant DNA cloning vectors and transformants of the present invention have broad utility and help fill the need for suitable cloning vehicles for use in streptomycetes and related organisms. Moreover, the ability of the present vectors to confer resistance to antibiotics also provides a functional means for selecting transformants. This is important because of the practical necessity for determining and selecting the particular cells that have acquired vector DNA. Additional DNA segments, that lack functional tests for their presence, can also be inserted into the present vectors and then transformants containing the non-selectable DNA can be isolated by appropriate antibiotic selection. Such non-selectable DNA segments can be inserted at any site, except within regions necessary for plasmid function, maintainance, and replication, and include, but are not limited to, genes that specify antibiotic modification enzymes, antibiotic resistance, antibiotic biosynthesis, and regulatory genes of all types.

The antibiotic resistance-conferring vectors of the present invention are also useful for insuring that linked DNA segments are stably maintained in host cells over many generations. These genes or DNA fragments, covalently linked to an antibiotic resistance-conferring fragment and propagated either in streptomycetes or in E. coli, are maintained by exposing the transformants to levels of antibiotic that are toxic to non-transformed cells. Therefore, transformants that lose the vector, and consequently any covalently linked DNA, cannot grow and are eliminated from the culture. This is particularly important in large scale fermentation where the maximum efficiency of product expression is desired. Thus, the vectors of the present invention can stabilize and maintain any DNA sequence of interest unless the cloned DNA or an expressed product is lethal to the host cell.

The cloning vectors and transformants of the present invention provide for the cloning of genes to improve yields of various products that are currently produced in streptomycetes and related cells. Examples of such products include, but are not limited to, streptomycin, tylosin, cephalosporins, actaplanin, avoparcin, narasin, monensin, apramycin, tobramycin, erythromycin, tetracycline, chloramphenicol, vancomycin, teichomycin, and the like. The present invention also provides selectable vectors that are useful for cloning, characterizing, and reconstructing DNA sequences that code for commercially important proteins such as, for example, human insulin, human proinsulin, glucagon, interferon, human growth hormone, avian growth hormone, bovine growth hormone, porcine growth hormone, interleukin I, interleukin II, and the like; for enzymatic functions in metabolic pathways leading to commercially important processes and compounds; or for control elements that improve gene expression. These desired DNA sequences include, but are not limited to, DNA that codes for enzymes that catalyze synthesis of derivatized antibiotics such as, for example, streptomycin, cephalosporins, tylosin, actaplanin, avoparcin, narasin, monensin, apramycin, tobramycin, tetracycline, chloramphenicol, erythromycin, teichomycin, and vancomycin derivatives, or for enzymes that mediate and increase bioproduction of antibiotics or other products.

The capability of inserting, stabilizing, and shuttling the aforementioned DNA segments into streptomycetes and E. coli allows for easy recombinant genetic manipulation for increasing the yield and availability of antibiotics that are produced by streptomycetes. In addition since the ~1.4 kb BclI-Sau3A replicon fragment of plasmid pHJL251 produces an ultrahigh copy number plasmid, almost any DNA sequence that is poorly transcribed or translated, can be readily cloned into the present vectors and shuttled between streptomycetes and E. coli.

Streptomycetes are reported to have very high percentages (69 to 73%) of guanine plus cytosine (G +C) in their genome. They have also been shown to exhibit codon usage patterns for protein expression that maximize the G +C content in the third, and to a lesser extent, the first position in a codon. The SCP2* minimal replicon nucleotide sequence of the present invention is disclosed in claim 1. Complete sequence analysis revealed numerous open reading frames of various lengths of amino acids. Inspection of this sequence reveals two potential initiation signals, both reading in the same frame. These ATG codons are located at nucleotide positions 1068 and 1077, numbered in accordance with claim 1. The G +C content for the third and first nucleotide positions are 91% and 68%, respectfully, when the ATG codon at position 1068 is utilized. Thus, the present replicon sequence conforms with the literature on streptomycetes proteins.

One skilled in the art will recognize upon analysis of the minimal replicon sequence that additional interesting features of the present sequence include inverted complementary sequences, direct repeated sequences, and possible Z-DNA sequences with the potential for left-handed helical conformation.

*Escherichia coli* K12 C600R$_k$—M$_k$—/pJL192 (NRRL B-15040), which provides the starting material for constructing many of the present vectors, can be cultured in a number of ways using any of several different media. Carbohydrate sources which are preferred in a culture medium include, for example, glucose and glycerol, and nitrogen sources include, for example, ammonium salts, amino acid mixtures, and peptones. Nutrient inorganic salts are also incorporated and include the customary salts capable of yielding magnesium, sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

*E. coli* K12 C600R$_k$—M$_k$—/pJL192 can be grown under aerobic culture conditions over a relatively wide pH range of about 6.5 to 7.5 at temperatures ranging from about 25° to 42° C. For the production of plasmid pHJL192 in the greatest quantity, however, it is desirable to start with a culture medium at a pH of about 7.2 and maintain a culture temperature of about 37° C. Culturing the *E. coli* cells under the aforementioned conditions, results in a reservoir of cells from which the plasmid pHJL192 is isolated by techniques well known in the art.

The following examples further illustrate the invention disclosed herein. Many of the procedures used in the construction of the present invention are set out below. Explanations of the procedures are provided in the examples where appropriate.

EXAMPLE 1

Culture of *E. coli* K12 C600R$_k$—M$_k$—/pJL192 and Isolation of Plasmid pHJL192

A single bacterial colony of *E. coli* K12 C600R$_k$—M$_k$—/pJL192 (NRRL B-15040) was inoculated into LB medium which contains, per liter aqueous solution, 10 g Bacto tryptone, 5 g Bacto yeast extract and 10 g NaCl (pH 7.5) with 25 µg/ml of ampicillin according to conventional microbiological procedures. The culture was incubated at 37° C overnight. The following morning, 10 ml of M9 medium (Miller, 1979, Experiments in Molecular Genetics, Cold Spring Harbor Laboratories, Cold Spring Harbor, N.Y.) supplemented with 1 mM MgSO$_4$, 0.2% glucose, 0.3–0.4% CAA (casamino acids, Difco), 2 µg/ml Bl (thiamine-HCl, Sigma) and additives were inoculated with 0.1 ml of the overnight culture. The culture was incubated with vigorous shaking at 37° C. overnight and the next morning samples of the overnight culture were inoculated at dilutions of 1/10 to 1/50 into 500 ml of the supplemented M9 media and incubated with vigorous shaking at 37° C. for 2.5 to 3 hours. The turbidity of the culture measured with the blue filter was approximately 300 to 400 Klett units. Chloramphenicol (150–175 µg/ml) was added to the culture and incubation with vigorous shaking was continued overnight.

The bacterial cells were harvested by centrifugation at 7500 rpm for 5 minutes at 4° C. and then washed twice with 200 ml of SV ( 0.15 M NaCl, 0.1 M Na-EDTA pH 8.0). The pellet was resuspended in 10 ml/gm wet weight TS solution (25% sucrose, 50 mM Tris, pH 8) and placed on ice. To this suspension, 2 ml/gm wet weight of lysozyme (5 mg/ml in 50 mM Tris-HCl pH 7.8) was added and left to chill on ice for 5 minutes. Next, 4 ml/gm wet weight of 0.25 M EDTA pH 8.0 was added and chilled for another 5 minutes. Upon the addition of 16 ml/gm wet weight lysis solution ( 0.4% deoxycholate, 1% Brij 58, 50 mM Tris and 0.0625 M EDTA, pH 8) the mixture was incubated at 37° C. for 15–30 minutes. The DNA was recovered by centrifugation in a Sorvall SS34 rotor at 21,000 rpm for 15–30 minutes at 4° C. The supernatant was saved and 0.1 vol. of 3 M NaOAc, at pH 8 and 0.64 volumes isopropanol were added to the supernatant. The DNA was centrifuged at 10,000 rpm for 10 minutes at 4° C., whereupon the pellet was resuspended in 0.1 volume TE (10 mM , 1 mM EDTA pH 8). The plasmid DNA was purified by centrifugation to equilibrium in cesium chloride density gradients containing propidium diiodide according to known techniques.

EXAMPLE 2

Construction of Intermediate Plasmids pHJL120 and pHJL121

A. EcoRI Digestion of Plasmid SCP2*

About 150 µl (5.7 µg) of plasmid SCP2* DNA (NRRL 15041), 1 µl water, 2 µl of EcoRI (containing 20 BRL units) restriction enzyme*, and 17 µl EcoRI reaction mix were incubated at 37° C. for 2.5 hours. This reaction was terminated by incubation at 60° C. for 10 minutes. In all of the following examples, digestion with restriction enzymes used the conditions recommended by the commercial supplier. The vector fragments used in ligation were routinely digested with calf intestine alkaline phosphatase (Ciap) to remove the terminal phosphate and prevent self ligation. Reaction with T4 DNA ligase formed recombinant DNA molecules under standard reaction conditions (Dugaiczyk et al., 1975, *J. Mol. Biol.* 96:171). Restricted DNA was analyzed by agarose gel electrophoresis or polyacrylamide gel electrophoresis (Fishman and Hershberger, 1983, *J. Bacteriol.* 155:459). Fragment sizes were calculated from measurements with a digital tablet (Elder et al., 1983, *Anal. Biochem.* 128:223).

*Restriction enzymes and instructions can be obtained from the following sources:
New England BioLabs., Inc., 32 Tozer Road, Beverly, Mass. 01915
Boehringer-Mannheim Biochemicals, 7941 Castleway Drive, Indianapolis, Ind. 46250

Bethesda Research Laboratories Inc., 8717 Grovemont Circle, Gaithersburg, Md. 20760

The reaction was conventionally analyzed by agarose gel electrophoresis (AGE) to verify that restriction was complete. The DNA was precipitated with 0.1 volumes 3 M NaOAc pH 8.0, followed by two volumes 100% ethanol. The precipitation can be done either at −20° C. overnight or at −70° C. (on dry ice) for at least 15 minutes. The DNA precipitate was washed once with cold 70% ethanol, dried and resuspended in 50 μl TE (10 mM Tris, 1 mM EDTA pH 8.0).

B. EcoRI Digestion of Plasmid pBR325

The desired digestion was carried out in substantial accordance with the teaching of Example 2A except that plasmid pBR325, rather than plasmid SCP2*, was used. The resultant DNA was stored at 4° C. for subsequent use.

C. Ligation of EcoRI Digested Plasmids SCP2* and pBR325

About 40 μl of EcoRI digested plasmid SCP2* (from Example A), 10 μl of EcoRI digested plasmid pBR325 (from Example B), 10 μl of MgCl₂ (0.1 M), 10 μl of (NH₄)₂SO₄ (0.1 M), 10 μl ATP (2 mM) 0.1 μl of T4 DNA ligase, and 20 μl ligation mix (50 mM Tris-HCl pH 7.5, 10 mM β-mercaptoethanol, 1 mM EDTA, 50 μg/ml BSA) were incubated at 4° C. for 18 hours. The reaction was analyzed by AGE to verify appropriate ligation. The suspended DNA constituted the desired ~35.8 kb plasmids pHJL120 and pHJL121.

Figure 6:
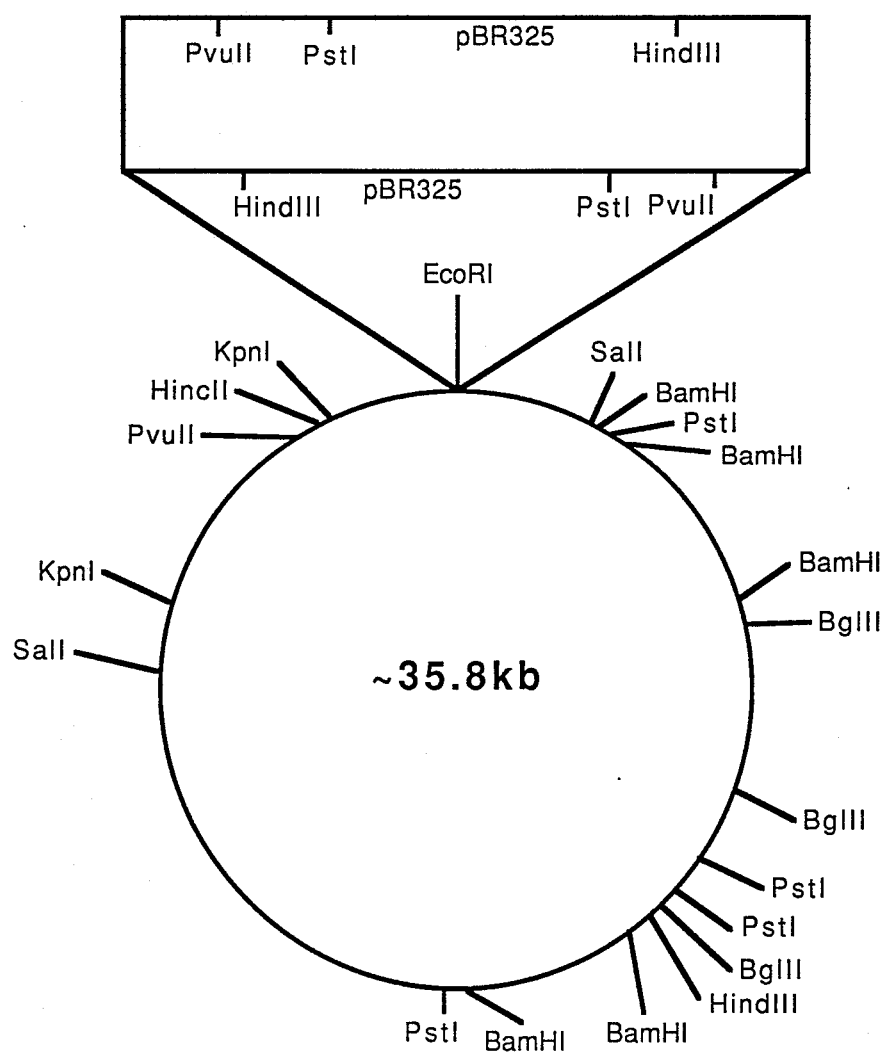
FIG. 6 is a restriction site map of plasmids pHJL120 and 121.

Recombinant plasmids of two orientations result because the plasmid pBR325 EcoRI fragment can be oriented in either direction. A restriction site map of each of plasmids pHJL120 and pHJL121 was determined (after isolation as disclosed in Example 1) and is presented in FIG. 6 of the accompanying drawings.

EXAMPLE 3

Transformation of E. coli

A. Preparation of Frozen Competent E. coli K12 C600R$_{k-}$M$_{k-}$

Fresh overnight cultures of E. coli K12 C600R$_{k}$—M$_{k}$—(E. coli), a strain widely available and on deposit with the ATCC under the accession number ATCC 33525, were subcultured 1:10 in fresh L-broth (disclosed in Miller, 1972) and grown at 37° C. for 1 hour. A total of 660 Klett Units of cells were harvested, washed with 2.5 ml of 100 mM NaCl, suspended in 2.5 ml of 150 mM CaCl₂ and incubated at room temperature for 20 minutes. The cells were harvested by centrifugation, resuspended in 0.5 ml of 150 mM CaCl₂-10% glycerol, chilled on ice for 3–5 minutes and frozen. The suspensions of cells were stored in liquid nitrogen until use. Preservation and storage did not adversely affect the viability or frequency of transformation by covalently closed circular DNA.

B. Transformation

The competent cells were thawed in an ice bath and mixed in a ratio of 0.1 ml of cells to 0.05 ml of DNA (12.5 μl of the sample disclosed in Examples 2C and 37.5 μl of .1XSSC (0.015 M NaCl, 0.0015 M Sodium Citrate at pH 7). The transformation mixture was chilled on ice for 20 minutes, heat shocked at 42° C. for 1 minute and chilled on ice for 10 minutes. The samples were then diluted with 0.85 ml of L-broth, incubated at 37° C. for 1.5 hours, spread on L-agar containing ampicillin (50 μg/ml) and incubated for 18 hours at 37° C. The resulting colonies of correct phenotype (ApR, TcR) were screened for plasmid size in substantial accordance with the method of in-the-well-lysis as described by Eckhardt et al., 1978, Plasmid 1:584. These resulting colonies constituted the desired E. coli K12 C600R$_{k}$—M$_{k}$—/pHJL120 and E. coli K12 C600R$_{k}$—M$_{k}$—transformants. The ampicillin resistant and tetracycline resistant colonies were isolated according to known procedures, cultured, and used to purify covalently closed circular DNA which was then conventionally identified by restriction enzyme and AGE analysis of the constitutive plasmids. The identified transformants were then used for subsequent production and isolation of plasmids pHJL120 and pHJL121 according to the teaching of Example 1 except that strains containing the desired plasmids were used instead of E. coli K12 C600R$_{k}$—M$_{k}$—/pJL192.

EXAMPLE 4

Construction of Intermediate Plasmid pHJL125

A. SalI Digestion of Plasmid pHJL121 and Isolation of ~10.2 kb SalI Fragment The desired digestion was carried out in substantial accordance with the teaching of Example 2 except that the reaction was stopped before digestion was complete, and plasmid pHJL121 and SalI restriction enzyme, rather than plasmid SCP2* and EcoRI, were used. The resultant SalI restriction fragments were not separated by preparative AGE but precipitated by standard ethanol precipitation. The restriction fragments were dissolved in TE buffer and immediately ligated.

B. Ligation of ~10.2 kb SalI Fragment of Plasmid pHJL121

Figure 7:
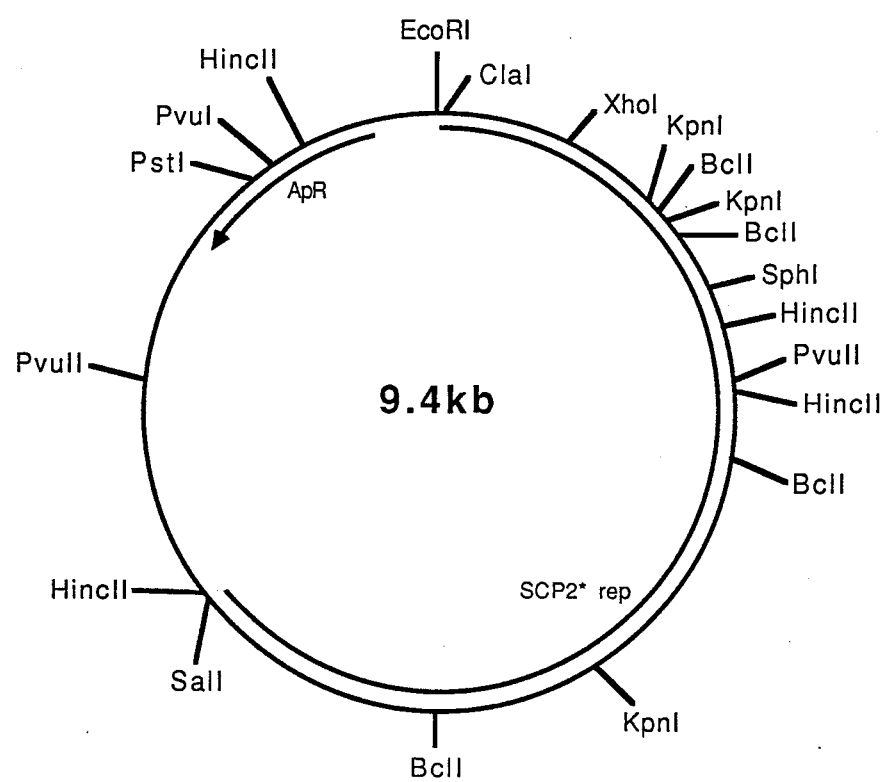
FIG. 7 is a restriction site and function map of plasmid pHJL125.

The isolated DNA was self-ligated and the resultant DNA constituted the desired plasmid pHJL125 plus 12 other plasmids that were subsequently isolated and shown to contain additional SalI restriction fragments of pHJL121. Plasmid pHJL125, which was conventionally isolated and contains an origin of replication from plasmid pBR325 and also the ~5.9 kb origin of replication-containing EcoRI-SalI fragment of plasmid SCP2*, was dissolved in TE buffer and stored at 4° C. for future use. A restriction site map of plasmid pHJL125 is presented in FIG. 7 of the accompanying drawing. The restriction site map was determined with plasmid DNA from transformed E. coli K12 C600R$_{k}$—M$_{k}$—.

EXAMPLE 5

Construction of Plasmids pHJL196 and pHJL197

Plasmid pHJL125 was digested with restriction enzymes EcoRI and SalI to completion. The ~5.9 kb EcoRI-SalI fragment containing the SCP2* replicon was gel-purified as taught in Example 6B (all partial digestions were performed using the teaching of Example 6B) and ligated to an ~7.5 kb EcoRI-partial SalI fragment of plasmid pHJL192.

The ligated material was used to transform competent E. coli cells, from which plasmid pHJL196 was isolated. The transformants were identified by their ampicillin resistant phenotype and by restriction enzyme analysis of plasmid DNA. The resultant cells were used to isolate their respective plasmid DNA in substantial accordance with the procedure of Example 1.

The ~1.1 kb BclI fragment derived from plasmid pIJ702 (ATCC 39155) contains the tsr gene which specifies resistance to thiostrepton in streptomycetes. This fragment was ligated to pHJL196 which had been partially digested with BamHI and then separated by AGE to isolate full-length linear molecules. Ligation of a BamHI fragment to a BclI fragment produces a junction that is no longer recognized by either enzyme. This junction is designated in the figures as "BamHI/BclI". The plasmid DNA was used to transform competent *E. coli* cells and the resulting transformants containing plasmid pHJL197 DNA were identified by restriction enzyme analysis of plasmid DNA. A restriction site and function map of plasmid pHJL197 is presented in FIG. 3 of the accompanying drawings.

EXAMPLE 6

Construction of Replicon Probe pHJL10

A. Construction of Intermediate Probe pHJL8

About 70 μl (20 μg) of plasmid pHJL197 were digested with 7 μl (70 units) of SalI restriction enzyme under partial digestion conditions to generate an ~3.6 kb fragment containing the neomycin resistance and thiostrepton resistance conferring genes. The ~3.6 kb SalI fragment was purified by AGE.

Complete SalI digestion and Ciap treatment of plasmid pKC7 (ATCC 37084) generated an ~5.25 kb fragment containing the kanamycin resistance conferring gene of Tn5, the ampicillin resistance conferring gene and replicon of plasmid pBR322. This ~5.25 kb SalI fragment was ligated to the ~3.6 kb SalI fragment under standard conditions and used to transform competent *E. coli* cells. Selection for the ApR and KmR transformants yielded isolates containing pHJL8. A restriction site and function map of plasmid pHJL8 is presented in FIG. 3 of the accompanying drawings.

B. Deletion of the Tn5 Gene

About 100 μl (24 μg) of pHJL8 were digested with 3 μl (10 units) of SalI restriction enzyme under partial digestion conditions. The restriction enzyme reaction was inactivated by increasing the temperature to 70° C. for 10 minutes. Next, ~10 μl (10 units) of EcoRI restriction enzyme were added and incubation continued until EcoRI digestion was complete. After ethanol precipitation, the DNA was resuspended in 100 μl of buffer [64 μl H₂O, 10 μl BSA.(1 mg/ml), 10 μl 10X Tris Acetate buffer, 4 μl T4 Polymerase (8 units/μl), and 3 μl of each dNTP (10 mM)]for 30 minutes at 37° C. The reaction was terminated by increasing the temperature to 70° C. for 10 minutes and the "filled-in" DNA was loaded on an 0.8% preparative agarose gel.

The separated fragments were located in the gel by staining with ethidium bromide and visualizing fluorescent bands with ultraviolet light. A slice adjacent to the desired ~7.5 kb band was made and DEAE-cellulose (Whatman DE-81) paper was placed in the slit. The DNA was electrophoresed until the DNA was completely bound to the paper. Upon removal, the paper was washed once in 100 mM KCl and 10 mM Tris-HCl, pH 8 and dispersed in 5 ml of elution buffer (1 M NaCl and 10 mM Tris-HCl, pH 8) by vigorous shaking. The paper was removed by filtration through siliconized pyrex wool and the DNA was either directly precipitated with 2 volumes ethanol or diluted by addition of 1 volume water, followed by ethanol precipitation. Either method of precipitation can be performed at −70° C. on dry ice for an hour or, alternatively, overnight at −20° C. The DNA was collected by centrifugation and the precipitate was resuspended in 200 μl TE at a concentration of 8 ng/μl.

About 100 μl of this DNA was precipitated with 10 μl 3M NaOAc and 220 μl ethanol and stored overnight at −20° C. The DNA was reprecipitated, dried, and resuspended overnight in 10 μl 5X kinase-ligase buffer (250 mM Tris HCl pH 7.8, 50 mM MgCl₂, 25 mM DTT, and 25% glycerol) with 25 μl 0.66 mM ATP, 1 μl ligase (1 unit/μl, Boehringer-Mannheim) and 14 μl H₂O. Approximately 25 μl of this ligation reaction was used to transform competent *E. coli* cells. The transformants were analyzed and pHJL10 was identified by restriction enzyme analysis.

EXAMPLE 7

Culture of *E. coli* K12 C600R$_k$—M$_k$—/pHJL224 and *E. coli* K12 C600R$_k$—M$_k$—/pHJL225 and Isolation of Plasmid DNA The desired culture and subsequent isolation of plasmids pHJL224 and pHJL225 were carried out in substantial accordance with the teaching of Example 1. The strains *E. coli* K12 C600R$_k$—M$_k$—/pHJL224 and *E. coli* K12 C600R$_k$—M$_k$—/pHJL225 are available to the public, as a preferred source and stock reservoir of their plasmids, under the accession numbers NRRL B-15988 and B-18052, respectively. A restriction site and function map of plasmid pHJL224 is presented in FIG. 4 and that of plasmid pHJL225 in FIG. 5 of the accompanying drawings.

EXAMPLE 8

Construction of an Ultrahigh Copy Number Shuttle Vector

About 35 μl (17 μg) of plasmid pHJL224 were digested with KpnI and BamHI restriction enzymes under standard conditions. The ~1.4 kb KpnI-BamHI replicon fragment was isolated by AGE and recovered as described in Example 6B.

Figure 8:
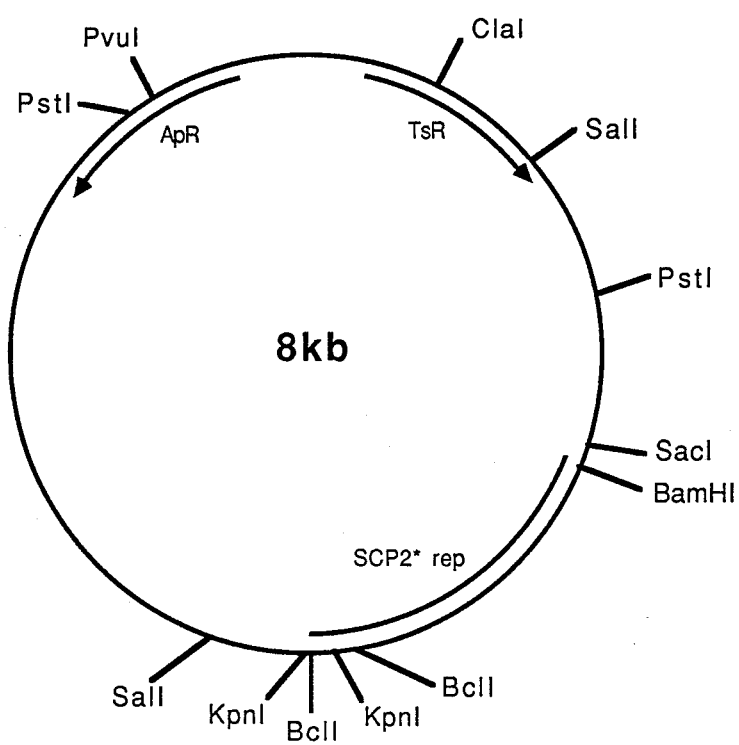
FIG. 8 is a restriction site and function map of plasmid pHJL236.

Plasmid pHJL10 was similarly digested with KpnI and BamHI to remove a 0.755 kb KpnI-BamHI fragment contained within the neomycin resistance gene. The ~1.4 kb replicon fragment was ligated to KpnI-BamHI-digested pHJL10 and the ligated mixture was used to transform *S. lividans* TK23 according to the teaching of Example 10. The transformants were identified by their thiostrepton resistant phenotype and by restriction enzyme analysis of their plasmid DNA. The resultant cells were used to isolate plasmid pHJL236. The plasmid DNA was transformed into competent *E. coli* cells and the transformants were identified by their ampicillin resistant phenotype. The transformants can then be used to isolate plasmid DNA. Plasmid pHJL236 does not give stable transformants in *S. griseofuscus* even though it yields transformants with ultrahigh levels of plasmid DNA in *S. lividans* TK23. A restriction site and function map of plasmid pHJL236 is presented in FIG. 8 of the accompanying drawings.

EXAMPLE 9

Transformation of *Streptomyces griseofuscus*

A. Growth of Cultures for Preparation of Protoplasts

A vegetative inoculum was conventionally prepared by growing *S. griseofuscus*, a strain deposited and made part of the permanent stock culture collection of the American Type Culture Collection, Rockville, Md. 20852, from which it is available to the public under the accession number ATCC 23916, under submerged conditions for 20 hours at 30° C. in TSB* supplemented with 0.4% glycine. The procedure for protoplasting *S. griseofuscus* is time-consuming and is generally performed as follows. Streak out *S. griseofuscus* on a plate containing YMX agar (0.3% yeast extract, 0.3% malt extract, 0.2% dextrose and 2% agar). Approximately 48 hours later, inoculate a single bacterial colony into 10 ml TSB; homogenize and incubate at 30° C. overnight. Next, homogenize 4 ml of the overnight culture and add 100 ml TSB supplemented with ,0.4% glycine and incubate overnight at 30° C. Repeat this procedure the following afternoon using fresh overnight culture. The following morning, add 50 ml of 50% (v/v) glycerol to the culture and freeze at −20° C. The frozen cells can be stored for six months and used for transformation. Thaw the frozen cells by placing the tube at room temperature in a beaker of water. Harvest the cells in a bench top centrifuge and wash three times in 10 ml of 10.3% sucrose. Resuspend the cell pellet in 10 ml of P medium (Hopwood and Wright, 1978, *J. Molecular and General Genetics* 162:307) supplemented with lysozyme (1 mg/ml) and incubate at 30° C. for 2 hours. Centrifuge to pellet the protoplasts and wash the pellet three times in 10 ml P medium, vortexing and pipetting the pellet into solution at each wash. Resuspend the final pellet in 2 ml P medium for subsequent transformation.

*Trypticase soy broth is obtained from Difco Laboratories, Detroit, Mich. or Baltimore Biological Laboratories, P.O. Box 243, Cockeysville, Md. 21031.

B. Transformation

About 10 μl of plasmid DNA in ligation buffer and about 150 μl of *S. griseofuscus* protoplasts were mixed slightly in a test tube. To this mixture about 101 μl 50% PEG 1000 (polyethylene glycol, Sigma) in P medium were added and pipetted to mix. After a 1–2 minute wait, P medium was added to bring the volume up to 1 ml. The transformed cells were plated on R2 medium and incubated overnight at 30° C. The regenerating protoplasts were overlayed with 3 ml R2 overlays containing 400 μg/ml thiostrepton and incubated at 30° C. for 4 days. The resulting *S. griseofuscus*/pHJL224 thiostrepton resistant colonies were isolated according to known procedures, cultured, and then conventionally identified in accordance with the teaching of Example 9C. The transformant culture was used for subsequent production and isolation of plasmid DNA.

Analysis of *S. griseofuscus* Transformants

The resultant transformants were cultured on YMX agar supplemented with thiostrepton (40 μg/ml) to obtain single colonies. These colonies were used to inoculate 10 ml TSB cultures containing thiostrepton (40 μg/ml). The cultures were homogenized and grown overnight at 30° C. in a rotary shaker.

The culture was homogenized and added to 200 ml TSB and 0.4% glycine supplemented with thiostrepton (40 μg/μl) and grown one to two days at 30° C. The cells were harvested in a Sorvall GSA rotor at 10,000 rpm for 15 minutes. The cells were resuspended in 100 ml TE containing 25% sucrose and lysozyme (5 mg/ml). After incubation at 37° C. for one hour, 50 ml of 0.25 M NaEDTA, pH 8.0 was added. 25 ml samples were transferred to Sorvall tubes containing 1 ml 20% w/v SDS (sodium dodecyl sulfate) and mixed gently at room temperature for 20–30 minutes to lyse the cells. After 8 ml of 5 M NaCl were added, the lysed material was mixed gently at room temperature for 30 minutes and then put on ice for 1½ hours. The cellular debris was removed by centrifugation in a Sorvall rotor at 15,000 rpm for 20 minutes. The supernatant was collected and the DNA precipitated with 0.64 vol. isopropanol and centrifuged for 20 minutes at 10,000 rpm. The supernatant was decanted and the DNA pellet was air dried and then resuspended in 10 ml TE buffer where it was purified by CsCl equilibrium gradients as taught in Example 1.

EXAMPLE 10

Transformation of *S. lividans*

The desired constructions were individually made, selected, and recovered in substantial accordance with the teaching of Example 9 except that *Streptomyces lividans* TK23, rather than *S. griseofuscus*, was used. *S. lividans* is an old and well-known strain which is available to the public under the accession number NRRL B-15826 which is on deposit and made part of the Northern Regional Research Laboratory, Peoria, Ill. 61604. In addition, the media for protoplasting and growing *S. lividans* and the preparation of protoplasts and transformation are as described in International Publication (of International Patent Application No. PCT/BG79/00095) No. W079/01169, Example 2. The identified transformants were then used for subsequent production and isolation of plasmid pHJL236 according to known procedures essentially as taught in Example 9C.

EXAMPLE 11

Construction of Ultrahigh Copy Number Plasmid pHJL241

Figure 9:
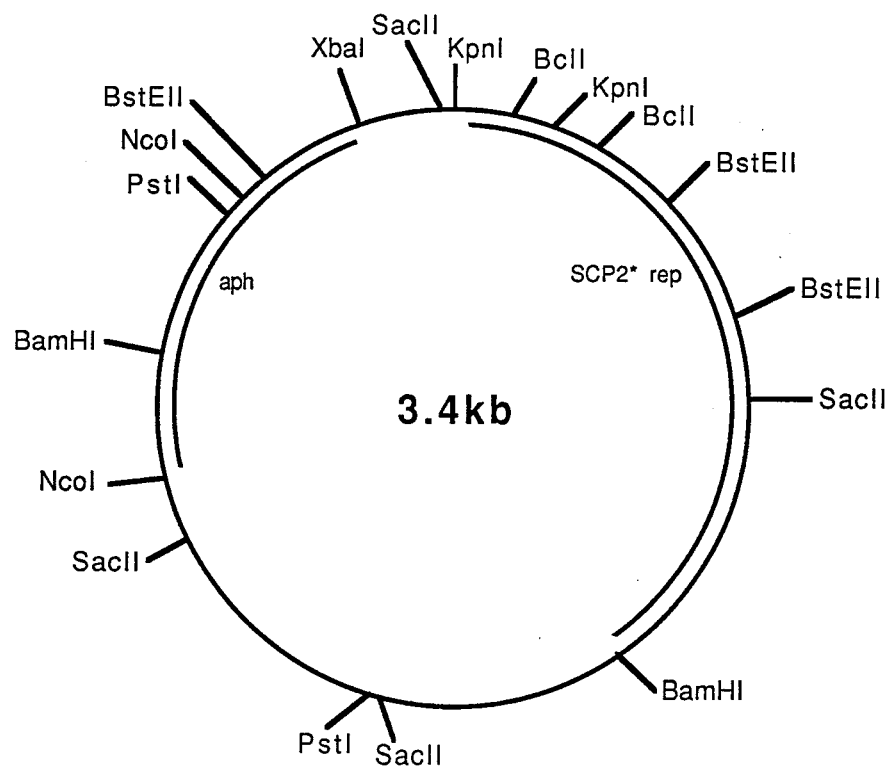
FIG. 9 is a restriction site and function map of plasmid pHJL241.

Plasmid pHJL241 was constructed by ligating the ~1.4 kb KpnI-BamHI replicon fragment of pHJL224 (isolated in Example 7) to the ~1.9 kb KpnI-partial BamHI fragment of plasmid pHJL196 (from Example 5). The ligated material was used to transform *S. lividans* TK23 in substantial accordance with the teaching of Example 10, with the substitution of plasmid pHJL241 DNA for pHJL236 DNA. In addition, neomycin at 50 μg/ml in the R2 overlay was used to select for transformants, rather than thiostrepton. A restriction site and function map of plasmid pHJL241 is presented in FIG. 9 of the accompanying drawings.

PAGE (polyacrylamide gel electrophoresis) was used to examine total protein of *S. lividans* TK23/pHJL241, as well as that of *S. lividans* TK23/pHJL197. *S. lividans* TK23 containing pHJL241 produces much more of the 31–33 kd (kilodalton) aminoglycoside phosphotransferase responsible for neomycin resistance than *S. lividans* TK23/pHJL197. Therefore, *S. lividans* TK23/pHJL241 is the preferred host to purify aminoglycoside phosphotransferase.

EXAMPLE 12

Construction of Intermediate Plasmid pHJL250

About 100 μl (40 μg) of plasmid pHJL236 from *S. lividans* TK23 were digested with BamHI and BclI restricton enzymes under standard conditions. The BamHI-BclI fragments were ligated to the ~1.1 kb BclI fragment containing the tsr gene (isolated in Example 5).

*S. lividans* TK23 was transformed with the ligation mixture and thiostrepton resistant transformants containing plasmid pHJL250 were subsequently analyzed by restriction enzyme analysis.

EXAMPLE 13

Construction of Ultrahigh Copy Number Plasmid pHJL251

Because plasmid pHJL250 contained several copies of the 159 bp BclI fragment from the left end of the replicon (refer to FIG. 1), ~14 μl (4 μg) of pHJL250 were digested with BclI restriction enzyme. The BclI-digested DNA solution was diluted with 80 μl of TE. About 4 μl were removed and ligated in a 40 μl reaction. The lower DNA concentration reduced ligations between the two DNA fragments and promoted recircularization with T4 DNA ligase.

Figure 10:
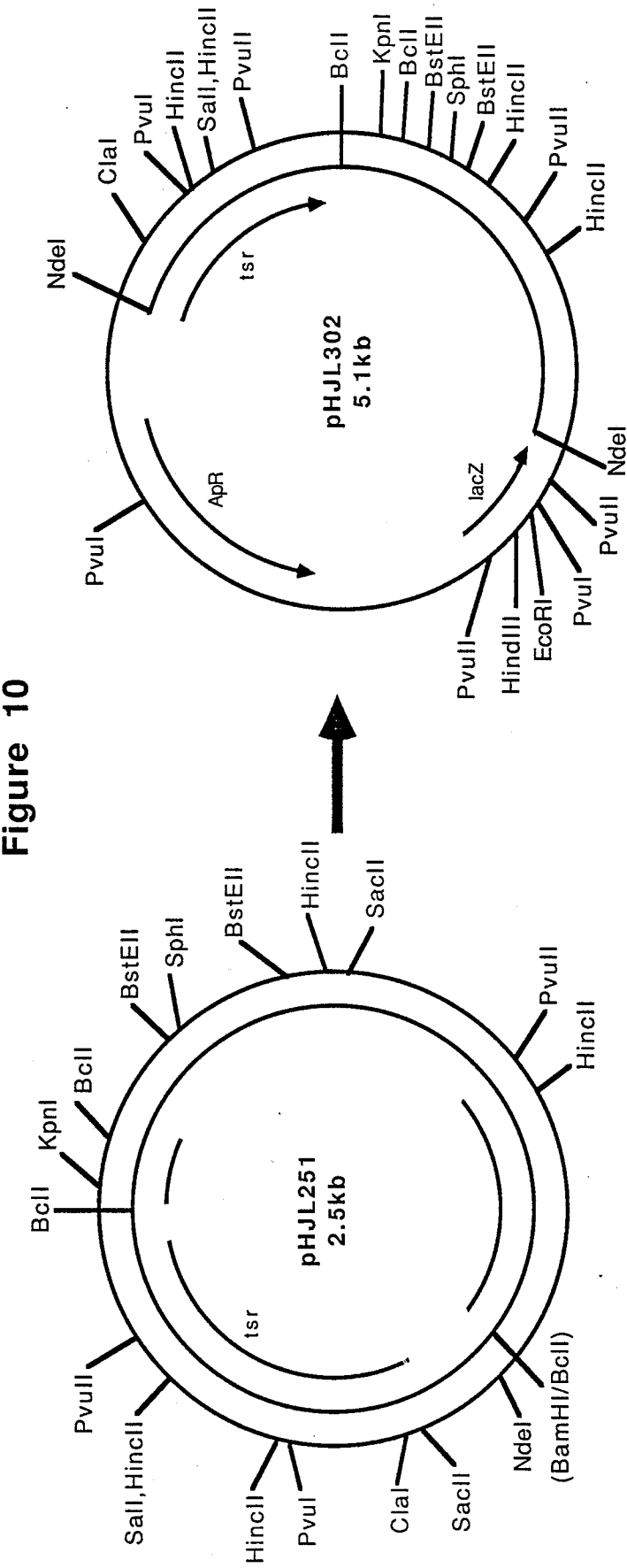
FIG. 10 illustrates the construction of plasmid pHJL302. DNA from different sources are identified as described in the description to FIG. 3 except that pUC19 is the *E. coli* plasmid. The arcs with a bar at each end identify deletions that render the plasmids incapable of replication in *S. lividans* TK23.

*S. lividans* TK23 was transformed with the ligation mixture and thiostrepton selected transformants containing pHJL251. A restriction site and function map of plasmid pHJL251 is presented in FIG. 10 of the accompanying drawings.

EXAMPLE 14

Construction of Moderate Copy Number Plasmids pHJL400 and pHJL401

A. NdeI Digestion of Plasmid pUC19

About 1 μg of plasmid pUC19 (Pharmacia, Inc., 800 Centennial Dr., Piscataway, N.J.) was digested to completion with NdeI restriction enzyme to generate linear vector fragments which were treated with Ciap.

Construction of Intermediate Plasmid pHJL399

About 35 μl (17.5 μg) of plasmid pHJL225 (isolated in Example 7) were digested with BamHI restriction enzyme to completion and the desired ~2.2 kb BamHI fragment containing the SCP2* replicon was purified by AGE. The 1.1 kb BclI fragment (isolated in Example 5) was ligated to the BamHI fragment to construct plasmid pHJL399.

Thiostrepton selected *S. lividans* TK23 transformants containing pHJL399. The transformants were analyzed by restriction enzyme analysis and the plasmid pHJL399 DNA was isolated for use in the construction of plasmids pHJL400 and 401.

C. NdeI Digestion of Plasmid pHJL399 and Ligation of Fragments

About 30 μl (1 μg) of plasmid pHJL399 were digested with NdeI restriction enzyme to completion. Since there is a unique NdeI site in plasmid pHJL399, a single, linear fragment was generated. T4 DNA ligase joined the pHJL399 NdeI fragment to NdeI-digested pUC19.

D. Transformation of *E. coli* JM109

*E. coli* JM109 cells (Yanisch-Perron et al., 1985, *Gene* 33:103) were made competent and transformed with the above ligation mix using the calcium chloride/rubidium chloride procedure essentially as described in Maniatis et al., 1982, Molecular Cloning, A Laboratory Manual, Cold Spring Harbor Laboratory, p. 252. Transformants were identified by resistance to ampicillin and formation of blue colonies on media containing X-gal and verified by restriction digests of plasmid DNA. Plasmids pHJL400 and pHJL401 differ only in the orientation of the NdeI restriction fragment of plasmid pHJL399. A restriction site and function map of plasmid pHJL400 is presented in FIG. 12 of the accompanying drawings. Both plasmids transform *S. griseofuscus* and *S. lividans* to thiostrepton resistance.

EXAMPLE 15

Transformation of *Streptomyces fradiae*

The construction of *S. fradiae*/pHJL400 and *S. fradiae*/pHJL401 were individually made, selected, and recovered in substantial accordance with the teaching of Example 9 except that *S. fradiae*, rather than *S. griseofuscus*, was used. *S. fradiae* is an old and well-known strain which is available to the public under the accession number ATCC 19609 which is on deposit and made part of the American Type Culture Collection. In addition, the TSB medium for protoplasting and growing *S. fradiae* was modified and contained only 0.2% glycine. *S. fradiae* transforms at very low frequencies because of an endogenous restriction system, therefore the number of transformants per μg of DNA is substantially less for *S. fradiae* hosts transformed with pHJL400 and pHJL401 than for *S. griseofuscus* or *S. lividans* hosts. However, plasmid DNA isolated from *S. fradiae* gives a high frequency of transformation when it is retransformed into *S. fradiae*.

EXAMPLE 16

Construction of Shuttle Vector pHJL302

About 10 μl (2 μg) of plasmid pHJL251 (constructed in Example 13) were digested with NdeI restriction enzyme to completion. The linearized vector fragment was then ligated to similarly digested pUC18.

The ligation mix was used to transform *E. coli* JM109 in accordance with the teaching of Example 14D and transformants were identified as taught in Example 14D and verified by restriction digests of plasmid DNA. A diagram of the construction of plasmid pHJL302 is presented in FIG. 10 of the accompanying drawings.

Plasmid pHJL302 DNA was used to transform strains of *S. griseofuscus*, *S. lividans*, and *S. fradiae* in accordance with the teaching of the previous examples. The vector transforms each host to thiostrepton resistance. In addition, the plasmid DNA was shown to be stably maintained in these transformants, unlike the previously described plasmid pHJL236 in *S. griseofuscus* and *S. fradiae*. Both plasmids pHJL302 and pHJL236 confer a moderately high copy number in *S. griseofuscus* and an ultrahigh copy number in *S. lividans*.

EXAMPLE 17

Sequencing Strategy of the Minimal Replicon

Figure 11:
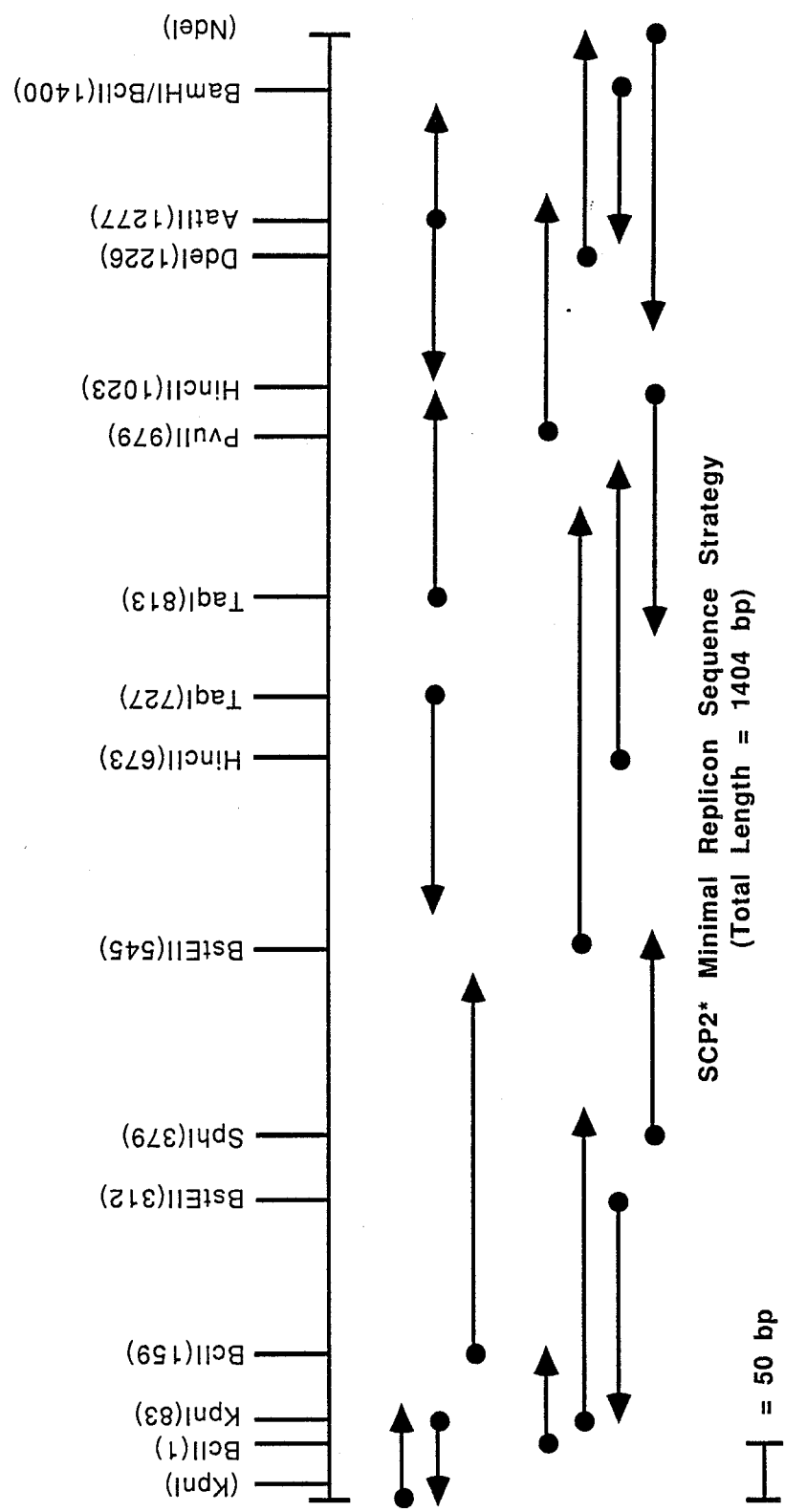
FIG. 11 is an illustration of the SCP2* minimal replicon sequencing strategy.

The SCP2* minimal replicon was sequenced in substantial accordance with the teaching of the Maxam and Gilbert protocol (1980, *Methods in Enzymology* 65(1):497). A physical map of the SCP2* minimal replicon is shown in FIG. 11 of the accompanying drawings. The complete 1404 bp sequence is contained within all of the plasmids herein that replicate in streptomycetes. The physical map shows restriction enzyme sites within the various DNA fragments used in the sequencing, as well as the sequencing strategy for the identification of the replicon. The dots indicate the sites of 5′-end labeling and the arrows show the distance and direction of sequencing.

We claim:

1. A recombinant DNA Streptomyces vector comprising:
   (a) a DNA sequence conferring a pleiotropic copy number phenotype and having at least the SCP2* minimal replicon of the approximately 1.4 kb BclI-Sau3A origin of replication-containing restriction fragment of the SCP2* replicon but no more than the approximately 2.2 kb origin of replication-containing BamHI restriction fragment of the SCP2* replicon, and
   (b) one or more DNA segments that convey resistance to at least one antibiotic when transformed into a sensitive, restrictionless host cell.

2. A recombinant DNA vector of claim 1 comprising a double-stranded deoxyribonucleic acid sequence for the SCP2* minimal replicon which confers a pleiotropic copy number to a host cell, wherein one strand of said DNA sequence is:

```
            10          20          30          40          50
5'-TGATCAATGG CGGGGGAATC GACCTCAGCC ACAGAAAGGC AACCCCTGCG 60          70          80          90         100
   GCGGGGGCGA CAACGGCGGC GGTACGGAGG TACCTCAGCC GCCCACCGGC 110         120         130         140         150
   AGGACGACGC TTCCTTCCTG CTTGTGGCCG GCCGAGGACA GCGTGCGGTC 160         170         180         190         200
   GCTAGGCGTG ATCAGGTGGC ATCAGTCGGG ACCCGCAAGC CCGCCAGGGC 210         220         230         240         250
   CGAGGACTCG CCGACCGTAG GCGCCGACGA GGACCAGGTG CGCAGGACCG 260         270         280         290         300
   CCGGCCTTCC CCGTAGAAGC TAAGAGCGGC CCGGTATGCC GGGCGGGTAG 310         320         330         340         350
   GAGTCCAGGG CGGTCACCAC GGTGTGCGCC GTGGTGCGCG AGTGACGGCG 360         370         380         390         400
   CGCGCCTTCT AGTGAAGAAG GGGCGCATGC TCTTGACCTG GTAAAACGCG 410         420         430         440         450
   CGGCTAAGCG GCTAAAAACC GCCGGTTACT GGGTCAAAAA TCGCCGCTTA 460         470         480         490         500
   GCTACCCACC GTGCGTCCCT CGTCGCGCCC GGTCGCCAGG AAGTCGCGTC 510         520         530         540         550
   ACCTATGCGT GTGACACGCG GACTAAGCGG CTGTTTTTCG GAGTGGTGAC 560         570         580         590         600
   CTGTTAGTTT CCTCTCGTAA GCGGCGGTTC ATCGGAGCTA AGGGGTCAAA 610         620         630         640         650
   AACCGCCCCT TAGCGCGAGG ATGGGAGAGG CGCGAGTGCC GACGAGGAAG 660         670         680         690         700
   CGCGGGCCGA ACATGGCCCT GGTCAACATG GACACCGGAG AGGCGGTGTC 710         720         730         740         750
   CGCCAGGCCG CGGACTCCGC ACCAGTTCGA CGGGAAGGGG TACACCTTGC 760         770         780         790         800
   AGGCCGTAGG CAGCGACGTC CCCCTGTACT CCCTCGGGCT GGCCGCAGCG 810         820         830         840         850
   GAGTGGGCGA CGCTCGAATG GCTCCGCGAA CACGGAGGCG CGGCCGGATA 860         870         880         890         900
   CGTCCCGGTC ACGCCCGAGG AGCTGGGCGA GGACGTCGGC GCCAGCAAGG 910         920         930         940         950
   ACACCTGCCG GAAGGCCCTT AACCGGCTGG TCAAGCTCGG GCTTGTGGTC 960         970         980         990        1000
   AAGCCGGGCC CGCGATCCGG CTCTTACCAG CTGAACCCCC TCCGATACTG 1010        1020        1030        1040        1050
   GGAGGGAGCC GGGAGCACGC AGGTCAACGC CTGCCGCCGC ATGGCGCCGC 1060        1070        1080        1090        1100
   CGCGTGTGGC CCCGGACGAC AAGGCCATGA CCAGGTCCGC CAGCAAGCCC 1110        1120        1130        1140        1150
   AAGACCATCC CGGCTACCCG CCGCCGCGCC GCAGGAGAGA CGCGATGACG
```

```
                    1160         1170         1180         1190         1200
            ACCATGCCCG   TAGAAGGCTT   CAACCCGGAG   CGCGACCTGA   CCGCCCCGTC 1210         1220         1230         1240         1250
            GCTGTACTCG   CCGAACCTGT   CCGCCGCTCA   GCACTGCACG   CTCGCGTGGG 1260         1270         1280         1290         1300
            TGGAGGACCA   CGGCGGCCTG   TTTGACGTCA   TCCCCGTACC   GGTCGAAACC 1310         1320         1330         1340         1350
            GTCGCCGAGG   ACTGCGGCAA   CTCCGTCTCC   ACGGTGCACG   AGGCTCTCGC 1360         1370         1380         1390         1400
            CCGCCTGGAG   GCCCTGAACC   TCCTCGTGCG   GACCTCCGCC   GGCCTCTACC

1405
            GGATC-3'
``` wherein
  A is deoxyadenyl,
  C is deoxycytidyl,
  G is deoxyguanyl, and
  T is thymidyl.

3. A vector of claim 1 wherein the pleiotropic copy number phenotype is ultrahigh.

4. A vector of claim 3 which is transformed into a sensitive, restrictionless *Streptomyces lividans* host cell.

5. The vector of claim 3 that is plasmid pHJL241.

6. The vector of claim 3 that is plasmid pHJL250.

7. The vector of claim 3 that is plasmid pHJL251.

8. The transformed host cell of claim 4 that is *Streptomyces lividans* TK23/pHJL241.

9. The transformed host cell of claim 4 that is *Streptomyces lividans* TK23/pHJL251.

10. The transformed host cell of claim 4 that is *Streptomyces lividans* TK23/pHJL236.

11. The transformed host cell of claim 4 that is *Streptomyces lividans* TK23/pHJL302.

12. A vector of claim 1 wherein the pleiotropic copy number phenotype is moderate.

13. A vector of claim 12 which is transformed into a sensitive, restrictionless *Streptomyces griseofuscus* host cell.

14. The transformed host cell of claim 13 that is *Streptomyces griseofuscus*/pHJL302.

15. The transformed host cell of claim 13 that is *Streptomyces griseofuscus*/pHJL236.

16. A vector of claim 1 which further comprises:
  (c) one or more restriction fragments comprising an *E. coli* replicon and one or more DNA segments that convey resistance to at least one antibiotic when transformed into a sensitive, restrictionless *E. coli* host.

17. The vector of claim 16 wherein the *E. coli* replicon-containing fragment is selected from the group consisting of fragments of plasmids pBR322, pBR325, pBR328 and pUC19.

18. The vector of claim 16 that is shuttle vector pHJL236.

19. The vector of claim 16 that is shuttle vector pHJL302.

20. A transformed restrictionless host cell comprising he recombinant DNA vector of claim 1.

21. The transformed host cell of claim 20 that is *Streptomyces fradiae*/pHJL302.

22. A moderate copy number streptomycete plasmid selected from the group consisting of plasmids pHJL225, pHJL400 and pHJL401.

23. The plasmid of claim 22 that is pHJL225.

24. The plasmid of claim 22 that is pHJL400.

25. The plasmid of claim 22 that is pHJL401.

26. A transformed restrictionless host cell comprising a moderate copy number streptomycete plasmid of claim 22.

27. The transformed host cell of claim 26 that is *Streptomyces griseofuscus*/pHJL225.

28. The transformed host cell of claim 26 that is *Streptomyces griseofuscus*/pHJL400.

29. The transformed host cell of claim 26 that is *Streptomyces griseofuscus*/pHJL401.

30. A replicon probe plasmid pHJL10.

* * * * *